United States Patent
Kidmose et al.

(10) Patent No.: US 10,285,615 B2
(45) Date of Patent: May 14, 2019

(54) PERSONAL EEG MONITORING DEVICE WITH ELECTRODE VALIDATION

(71) Applicant: WIDEX A/S, Lynge (DK)

(72) Inventors: Preben Kidmose, Maarslet (DK);
Michael Ungstrup, Allerod (DK);
Mike Lind Rank, Farum (DK)

(73) Assignee: WIDEX A/S, Lynge (DK)

( * ) Notice: Subject to any disclaimer, the term of this patent is extended or adjusted under 35 U.S.C. 154(b) by 1010 days.

(21) Appl. No.: 13/845,490

(22) Filed: Mar. 18, 2013

(65) Prior Publication Data
US 2013/0296731 A1    Nov. 7, 2013

Related U.S. Application Data

(63) Continuation-in-part of application No. PCT/EP2011/050733, filed on Jan. 20, 2011.

(51) Int. Cl.
*A61B 5/0484* (2006.01)
*A61B 5/00* (2006.01)
*A61B 5/048* (2006.01)

(52) U.S. Cl.
CPC ........ *A61B 5/0484* (2013.01); *A61B 5/04845* (2013.01); *A61B 5/6817* (2013.01);
(Continued)

(58) Field of Classification Search
None
See application file for complete search history.

(56) References Cited

U.S. PATENT DOCUMENTS 4,421,122 A * 12/1983 Duffy ............... A61B 5/0484
600/544
4,736,751 A * 4/1988 Gevins ............. A61B 5/0017
600/544
(Continued)

FOREIGN PATENT DOCUMENTS

WO    2006/009771 A1    1/2006
WO    2006047874 A1     5/2006
(Continued)

OTHER PUBLICATIONS

Qu, Hao, and Jean Gotman. "A patient-specific algorithm for the detection of seizure onset in long-term EEG monitoring: possible use as a warning device." (1997) Biomedical Engineering, IEEE Transactions on 44.2: 115-122.*
(Continued)

*Primary Examiner* — Sean P Dougherty
*Assistant Examiner* — Jairo H Portillo
(74) *Attorney, Agent, or Firm* — Sughrue Mion, PLLC

(57) ABSTRACT

A personal wearable EEG monitor (1) is adapted to be carried at the head of a person. The EEG monitor comprises an EEG sensor part having skin surface electrodes (3) for measuring EEG signals from said person. The EEG monitor comprises an EEG signal analyzer (5, 5') adapted for monitoring and analyzing the EEG signal. The EEG monitor (1) performs at least one of the following: providing a stimulus to the person, requesting the person to perform a stimuli creating act, or identifying a stimuli creating ambient sound. The EEG monitor comprises means for identifying an induced response from the EEG signal caused by the stimuli, and a classifier for deciding whether the skin surface electrodes receive EEG signals. The invention further provides a method of monitoring EEG signals of a person.

24 Claims, 10 Drawing Sheets

(52) U.S. Cl.
CPC .......... *A61B 5/6833* (2013.01); *A61B 5/6843* (2013.01); *A61B 5/048* (2013.01); *A61B 5/04842* (2013.01); *A61B 2560/0276* (2013.01)

(56) References Cited

U.S. PATENT DOCUMENTS

| | | | |
|---|---|---|---|
| 2004/0039422 A1* | 2/2004 | Russie | A61N 1/3712 607/9 |
| 2006/0049957 A1* | 3/2006 | Surgenor | A61B 5/0031 340/4.1 |
| 2007/0018809 A1* | 1/2007 | Reiter | A61B 5/0424 340/539.11 |
| 2007/0055114 A1* | 3/2007 | Viertio-Oja | A61B 5/0484 600/300 |
| 2007/0112277 A1 | 5/2007 | Fischer et al. | |
| 2007/0191727 A1* | 8/2007 | Fadem | A61B 5/0002 600/544 |
| 2007/0244407 A1 | 10/2007 | Osorio | |
| 2009/0312664 A1* | 12/2009 | Rodriguez Villegas | A61B 5/0476 600/544 |
| 2010/0185256 A1* | 7/2010 | Hulvershorn | A61N 1/36071 607/45 |

FOREIGN PATENT DOCUMENTS

| | | |
|---|---|---|
| WO | 2006/066577 A1 | 6/2006 |
| WO | 2007/047667 A2 | 4/2007 |
| WO | 2007/150003 A2 | 12/2007 |
| WO | 2009/100654 A1 | 8/2009 |
| WO | 2011000383 A1 | 1/2011 |

OTHER PUBLICATIONS

International Search Report and Written Opinion of the International Searching Authority for PCT/EP2011/050733 dated Jul. 19, 2011.

Communication from the Canadian Patent Office dated Feb. 29, 2016 in counterpart Canadian Patent Application No. 2,818,254.

Communication from the Korean Patent Office dated Feb. 24, 2016 in counterpart Korean Patent Application No. 10-2013-7021920.

* cited by examiner a)

b)

c)

PERSONAL EEG MONITORING DEVICE WITH ELECTRODE VALIDATION

RELATED APPLICATIONS

The present application is a continuation-in-part of application PCT/EP2011/050733, filed on 20 Jan. 2011, in Europe, and published as WO 2012097872 A1.

BACKGROUND OF THE INVENTION

1. Field of the Invention

The present invention relates to monitoring of EEG signals. The invention more particularly relates to a personal wearable EEG monitor adapted to be carried at the head of a person. The EEG monitor comprises an EEG sensor part having electrodes arranged on the skin surface of a person for measuring one or more EEG signals from said person. The EEG monitor further comprises an EEG signal analyzer adapted for having an EEG signal transferred from the EEG sensor part, and adapted for monitoring the EEG signal from the person wearing the device. The invention further relates to a method for monitoring EEG signals of a person.

Personal wearable EEG monitors are known for surveillance of EEG in order to detect imminent seizures, but could also be applied for long term EEG recording.

2. The Prior Art

Such personal wearable EEG monitors are known from WO 2007/150003 describing a system for long term EEG monitoring with implanted electrodes.

WO 2006/066577 describes a personal monitoring device for detecting the onset of hypoglycemia by analyzing an EEG signal obtained through implanted electrodes.

WO 2007/047667 describes EEG monitoring partly by application of an electrode in the ear canal. The application of auditory evoked potentials is also described.

It has been found that wearable personal devices for long term measurements of EEG-signals can be located in the region behind or in the ear of the user with several advantages. This location is ideal for physiologic, cosmetical and mechanical reasons.

A measurement of the EEG signal in the ear canal has the advantage of being protected against external electrical fields since the ear canal extends into the head which will shield the EEG electrodes partly. It is possible to obtain a very good fit between an earpiece holding the electrode and the ear canal, and thereby the contact between the skin and the electrode becomes less sensitive to movements and skin strain. Further to this, the ear itself, or part of it, may be used for attachment of the device. Many EEG signals are also available from the ear region.

Other examples of wearable EEG monitors could be hearing aids with EEG-feedback (e.g. the hearing aid is in some way adjusted according to information extracted from an EEG signal) and personal health monitoring devices. Examples of personal health monitoring devices could be hypoglycemia warning devices for persons with diabetes, and seizure warning devices for persons with epilepsy. Also continuous monitoring of the EEG signal for diagnostic or research purposes may be relevant.

The requirements and trade-offs between different characteristics for electrodes for EEG measurements in wearable personal devices are different from those for electrodes for clinical use, e.g. short term EEG monitoring of a patient in a hospital. Typical requirements for electrodes in wearable personal devices are, that they must be easy to put in place, they should not exert any stress on the skin (e.g. no strain of the skin), they must be comfortable and small (e.g. the size of a hearing aid), they must be cosmetically acceptable, addition of gel between skin and electrode should be avoided (i.e. dry electrodes), and in general no skin preparation should be necessary. These requirements compromise the signal acquisition properties and the reliability of the electrodes, as the requirements will make it more difficult to obtain a good electrical contact between skin and electrode. Thus electrodes designed for such devices have typically much larger impedances (e.g. in the hundreds of kilo Ohm range), larger variations in impedances, and are less reliable than electrodes for clinical use.

Traditionally electrodes for electrical bio-potential measurements, such as EEG, are validated by measuring the electrical impedance between two or more electrode elements. This method is feasible for clinical use and for electrodes with reasonably low impedances, e.g. less than a few hundred kilo Ohms. Measurement of electrical impedance has now been found not to be sufficiently reliable for electrodes with very large electrical impedance. This is because measuring the electrical impedance will only reveal if there is an electrical connection between two electrodes, but not if the electrodes are measuring an EEG signal. An electrical connection may just be due to a layer of dirt on the part holding the electrodes.

In long term monitoring of EEG-signals in wearable personal devices there is a need for validating the EEG signal measured by the electrodes, and for the reasons mentioned above there is a need for an alternative method to the electrical impedance method. The electrode validation must be easily performed by the user. Furthermore the electrode validation should preferably be an integrated capability of the device.

SUMMARY OF THE INVENTION

The invention, in a first aspect, provides a wearable EEG monitor adapted to be carried at the head of a person, said EEG monitor comprising an EEG sensor part having skin surface electrodes for measuring an EEG signal from said person, an EEG signal analyzer adapted for having an EEG signal transferred from said EEG sensor part, and adapted for monitoring the EEG signal from said person, EEG stimuli controlling means adapted for performing at least one of the following providing a stimulus to said person, requesting said person to perform a stimulus-creating act, identifying a potentially stimulus-creating ambient sound, EEG response detection means for identifying an induced response from the EEG signal caused by said stimulus, and a classifier for deciding based on said at least one induced response if said skin surface electrodes receive EEG signals of said person.

The term induced response refers to an EEG signal induced by a stimulus which is distinct from the otherwise spontaneous EEG signal. Examples of induced responses are listed in Table 1 below. One possible stimulus considered in the system described here is an auditory stimulus in a broad sense, and the measured signal could e.g. be an auditory evoked response.

Auditory evoked potentials can be used to trace the signal generated by a sound through the ascending auditory pathway. Thus the measured signal may include induced responses generated in the cochlea, the cochlear nerve, the cochlear nucleus, the superior olivary complex, the lateral lemniscus, the inferior colliculus in the midbrain, the medial geniculate body, or from the cortex. Thus an induced auditory response may reflect:

1) A direct and autonomous response to the acoustical signal in the processing of the stimulus in the auditory pathway;
2) A response caused by processing in the cortexes of the brain.

Whereas the first, referred to as an auditory evoked potential, is an innate response from the auditory pathway processing, the latter may require cooperation or certain acquired skills by the user.

To exploit induced responses of the first kind the acoustical signal typically has certain simple acoustical characteristic such as e.g. an amplitude modulation or a pitch sweep.

To exploit induced responses of the second kind the signal typically has more complex information, such as a series of syllables, words or even sentences containing instructions or sentences with syntactical errors.

The methodology of auditory evoked responses is well known in e.g. the area of research of the auditory pathways and in medicine for diagnostic use. Below, the use of induced responses for electrode validation is described with focus on a setup where a certain response is expected, and the presence of the expected response validates that the electrodes are measuring valid EEG signals.

The EEG sensor part is to be understood as the combined EEG electrodes whether these are placed together in a unit or connected only by wires. The EEG sensor part may or may not include signal acquisition means for collecting and preprocessing the EEG signal from the electrodes. If no induced response can be detected in the EEG signal, the reason may be that there is no, or a very bad, electrical connection between one or more electrodes and the skin surface. In that case a notification may be given in order for the person to rearrange the electrode.

The potentially stimulus-creating ambient sound could e.g. be a sudden sound after a period of relative silence. It could also be other sudden changes in the background sounds. The term potentially is used as there is no certainty that a sound identified also induces an EEG response.

In an embodiment of the EEG monitor the electrodes are dry electrodes, i.e. adapted to function without skin preparation, such as a gel between the electrode and the skin. Dry electrodes will have relatively higher impedance, and the validation of the electrodes, i.e. confirming that the electrodes actually receive an EEG signal, therefore becomes particularly important.

In an embodiment of the EEG monitor at least one electrode is adapted to be removable and arranged in an ear canal of said person. As outlined above the ear canal has several advantages for the measurement of an EEG signal. In a further embodiment two or more electrodes are arranged in the ear canal. An EEG monitor with at least one electrode in both ear canals of a person is also possible.

In an embodiment of the EEG monitor the EEG stimuli controlling means provides auditory stimuli to said person through a receiver or speaker in the monitor. This has the advantage that the person does not need to perform an active act in order to have a validation of the electrodes.

In an embodiment of the EEG monitor the EEG stimuli controlling means are adapted for identifying sounds from the surroundings capable of causing an induced response. This has the further advantage that the person will not even notice that the EEG electrodes are being validated.

In an embodiment of the EEG monitor the EEG stimuli controlling means are adapted for requesting said person to open and close the eyes. This will provide a very clear induced response.

The three different embodiments described for providing the EEG stimuli may be combined, such that e.g. the embodiment with opening and closing the eyes is applied when the electrodes have been arranged or rearranged on the person, and the embodiment identifying sounds from the surroundings is applied for controlling that the electrodes receive the actual EEG signal at regular intervals. If the person is in a silent acoustic environment, the EEG monitor may apply the embodiment where auditory stimuli are provided.

In an embodiment of the EEG monitor the stimulus is repeated at least two times for a validation of the electrodes. This will offer more reliability in the result.

In an embodiment of the EEG monitor at least one electrode adapted to be arranged in the ear canal is arranged on an ear-piece, said ear-piece being provided with a permanent shape fitting the ear canal of said person. Such an ear-piece made especially to the dimensions of the ear canal of the person to wear the EEG monitor will make it easy for the person to arrange the ear-piece in exactly the same position every time it is used. This ensures that the EEG signal is obtained from the same position every time the monitor is used. Thereby the EEG signals obtained in one time period will be comparable with EEG signals obtained in a different time period where the ear-piece has been removed and re-arranged between the two time periods. Providing the ear-piece with a permanent, customized shape also includes resilient materials making the ear-piece more comfortable to wear.

In an embodiment of the EEG monitor the monitor comprises a pad electrode arranged external to the EEG sensor part, where the pad electrode is adapted to be arranged on the head of the person to be monitored. Such a pad electrode can be used for special purposes such as obtaining specific EEG signals not available from the ear canal.

In an embodiment of the EEG monitor the monitor is adapted for testing the validity of the electrodes as a group. In an alternative embodiment the validity of the electrodes is tested pair wise. If all possible combinations of electrodes are tested pair wise, the validity of each individual electrode can be clarified.

In an embodiment of the EEG monitor the validation of electrodes by identifying an induced response is combined with measuring the electrical impedance between electrodes placed on the skin surface. This may also increase the reliability of the electrode validation.

In an embodiment the EEG monitor further comprises notification means for notifying said person if the EEG signal is not received. The person may then improve the positioning of the electrode part. In a further embodiment the EEG monitor comprises means for transmitting a wireless notification to an external unit in the event that the EEG signal is not received by the electrodes.

In a second aspect, the invention provides to a method for monitoring EEG signals of a person by an EEG monitor carried at the head of said person, said method comprising the steps of measuring one or more EEG signals from said person by an EEG sensor part having skin surface electrodes, transferring an EEG signal from said EEG sensor part to a processing unit having EEG signal processing means, monitoring the EEG signal from said person in said processing unit, causing an induced response in the EEG signal by performing at least one of the following: providing a stimulus to said person, requesting said person to perform a stimulus creating act, or identifying a stimulus creating ambient sound, identifying an induced response from the EEG signal caused by said stimuli, and deciding based on said induced response if said skin surface electrodes receive EEG signals of said person.

In an embodiment the method comprises the step of notifying said person if the EEG signal is not received by said electrodes.

In an embodiment the method comprises the step of identifying the specific electrodes receiving an EEG signal. Then the EEG signal can be monitored by these electrodes. In a further embodiment the method comprises the step of reconfiguring the EEG monitor to measure the EEG signal by selecting those electrodes receiving an EEG signal.

In an embodiment the method comprises repeating the steps of causing an induced response in the EEG signal and identifying an induced response from the EEG signal at time intervals either preselected or adjusted according to previous decisions if said electrodes receive an EEG signal. The urgency of predicting an imminent seizure for the person may also influence the selection of the time interval.

BRIEF DESCRIPTION OF THE DRAWINGS

Embodiments of the invention will now be explained in further detail with reference to the figures.

DETAILED DESCRIPTION

Figure 1:
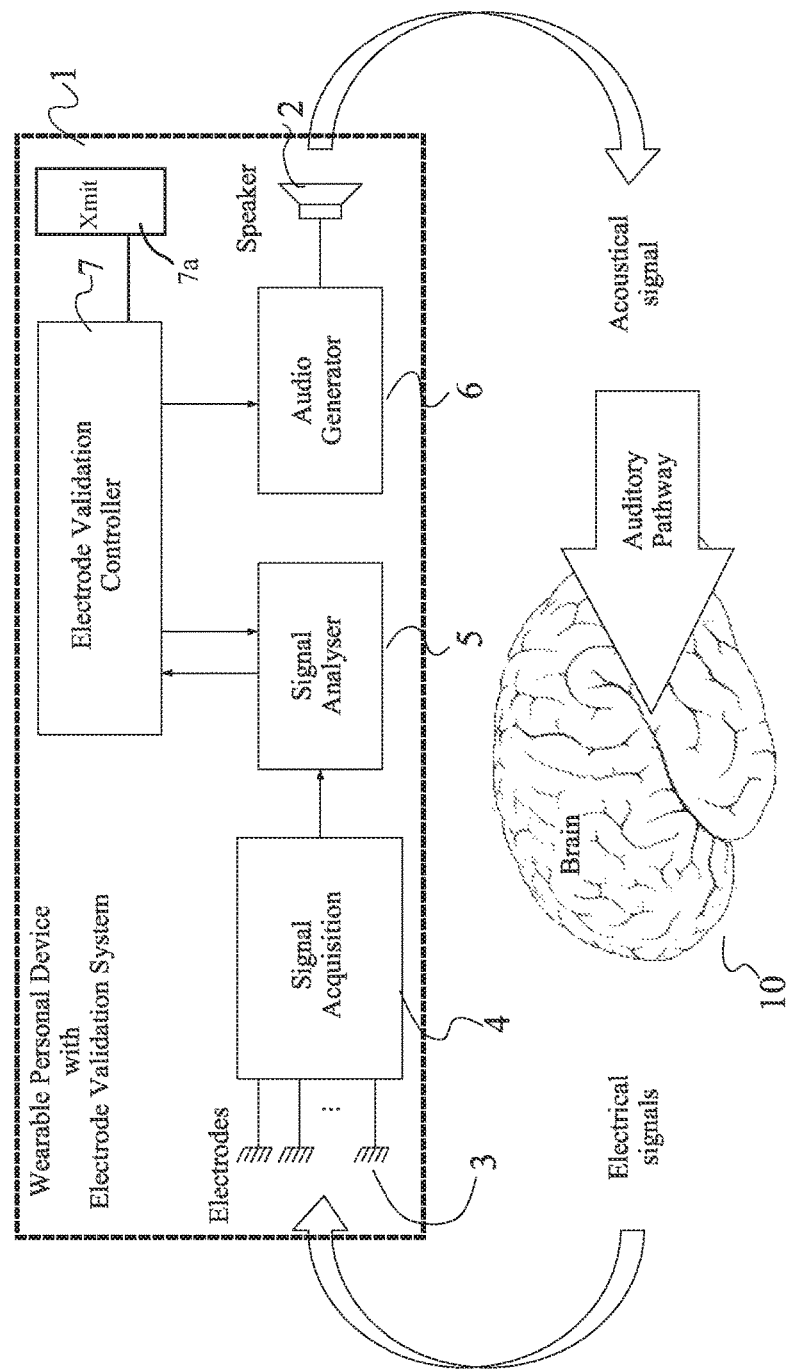
FIG. 1 illustrates a block diagram of a Wearable Personal Device incorporating an Electrode Validation System based on auditory evoked response caused by an audio stimulus generated by a speaker.

FIG. 1 shows a system for electrode validation and the measurement setup. The dashed box indicates the wearable personal device 1 with the electrode validation system. The device includes a speaker 2 that receives an electrical signal from an audio generator 6 and generates an acoustical signal. The acoustical signal is intended to lead to an induced EEG potential either directly by the sound alone, thereby obtaining an auditory evoked potential, or indirectly by guiding the person to perform an act causing an induced potential in the EEG signal. The device 1 further includes at least two electrodes 3 for measuring the EEG signal from the user's brain 10. The electrode validation system comprises signal acquisition means 4 for acquiring the EEG signal from the electrodes 3. The electrodes 3 form the EEG sensor part. The signal acquisition means 4 could also have been placed as part of the EEG sensor part. The signal is sent to an EEG signal analyzer 5 where the surveillance of the EEG signal is performed. An electrode validation controller 7 compares acquired signals from the electrodes 3 with the timing of acoustical signals given by the audio generator 6 and speaker 2. Based on this the electrode validation controller 7 decides if the signal acquired by the electrodes is an EEG signal. The classifier deciding if the electrodes 3 detect an induced response, and thereby receive the EEG signal, is part of the electrode validation controller 7.

The EEG stimuli controlling means corresponds in the embodiment of FIG. 1 to the audio generator 6. The EEG response detection means are part of the electrode validation controller 7 and identifies induced response in the EEG signal received from the EEG signal analyzer 5. The decision on whether to notify the person wearing the EEG monitor is made in the electrode validation controller 7. The decision can be based on preselected criteria. Such criteria may be that if a stimulus does not elicit an induced response in the EEG signal, a notification could be given directly to the person. Otherwise, a test could be performed again e.g. by application of a different type of stimulus. The monitor may further include a transmitter 7a for transmitting a wireless notification to an external unit in the event that the EEG signal is not received by the electrodes.

The induced potential amplitudes are in general low compared to the spontaneous potential amplitudes and therefore it is usually necessary to time-average the signals from several stimulations. Because the spontaneous EEG signal by definition is independent of the stimulus, time-averaging can be obtained by adding several time frames of the signal synchronized to respective stimuli. The power of the induced response part of the signal increases with 3 dB every time the number of time averages is doubled. I.e. 3 dB can be obtained at two time-averages, 6 dB can be obtained by four averages, and 9 dB can be obtained by eight averages.

Examples of EEG induced response schemes suitable for electrode validation are listed in Table 1. Two of the examples in Table 1 are based on so called mismatch negativity (MMN) or oddball paradigm. The MMN or oddball paradigm is a technique used in general to explore event-related potentials (ERP). The event-related potential is elicited by an unexpected change in a sequence of stimuli. For example, a deviant (d) sound with low probability can be mixed among a series of standard (s) sounds with high probability (e.g., s s s s s s d s s s s s s d s s s . . . ). Simple sounds will be applied for this, e.g. a number of "bib" sounds interrupted by a single "bob" sound. Such sequence is called an oddball sequence. The deviant sound can differ from the standard sounds in one or more perceptual features such as pitch, duration, or loudness. The event-related potential can be elicited regardless of whether the subject is paying attention to the sequence or not. During the oddball sequence, a person can be reading or watching a silent subtitled movie, yet still show a clear MMN.

Figure 2:
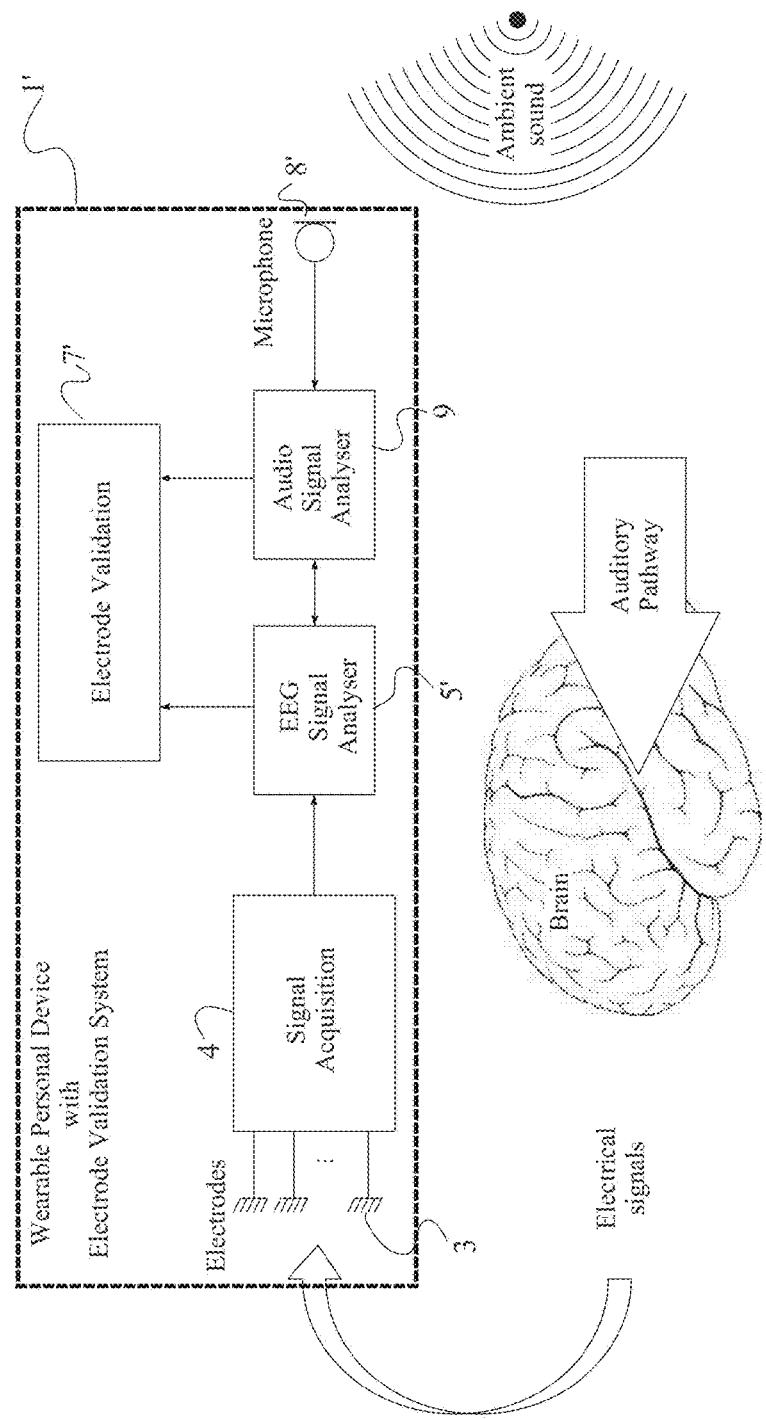
FIG. 2 illustrates the block diagram FIG. 1, with the change that the audio stimulus is from the users sound environment.

FIG. 2 shows a system for electrode validation based on ambient sound environment and the measurement setup for this electrode validation. The dashed box indicates the wearable personal device 1' with the electrode validation system. The device 1' includes a microphone 8' that measures the ambient sound environment, and an audio signal analyzer block 9 for identifying sounds in the surroundings which could cause an induced response. The device 1' further includes at least two electrodes 3 for measuring the EEG signal from the user's brain, and an EEG signal analyzer block. The electrode validation system comprises signal acquisition means 4 for acquiring the EEG signal from the electrodes 3. The signal is sent to a signal analyzer 5'. An electrode validation controller 7' compares acquired signals from the electrodes 3 with acoustic signals recorded by the microphone 8', in order to decide if sounds from the surroundings may cause induced responses, and finally decide if the signals acquired by the electrodes 3 are EEG signals.

The EEG stimuli controlling means corresponds in the embodiment of FIG. 2 to the audio signal analyzer 9.

Alternatively to generating the audio-stimuli by the device as shown in FIG. 1, the electrode validation may be based on the ambient sound-environment as shown in FIG. 2. In this system the device measures both the EEG from the user's brain, and the ambient sound environment by a microphone integrated in the device. The EEG signal analyzer 5' and the audio signal analyzer 9 blocks may for instance comprise algorithms for envelope-spectrum estimation, and the electrode validation block may comprise algorithms to exploit the dependencies between the EEG-envelope spectrum and the audio-envelope spectrum. An advantage of this system is that the electrode test may be running at all times and without disturbing the users with audio signals. Examples of induced response schemes suitable for electrode validation are given in table 1, where each scheme is described in detail.

TABLE 1

Examples of induced response schemes

| Scheme | Description |
| --- | --- |
| Brainstem Auditory-Evoked Potentials (BAEP) or Auditory Steady State Response (ASSR) | In BAEP the stimuli are typically click or tones. Click stimuli can for instance be 8-10 clicks/sec. Tones can be on/off modulated; or for instance a 500, 1000, 2000, or 4000 Hz carrier amplitude modulated (AM) with modulation rate of e.g. 40-100 Hz. The modulator signal frequency and harmonics thereof can be detected in the EEG signal. |
| Harmonic oddball | An oddball sequence comprising harmonic (h) and disharmonic (d) sounds (e.g.: h h h h h h h h d h h h h h h d h h h h d h h h . . .). An ERP can be detected in the EEG. |
| Linguistic oddball | Linguistic anomalies or violations of syntactic or semantic rules in the acoustic stimuli cause ERPs. An ERP can be detected in the EEG. |
| Open/closed eyes | Alpha waves are oscillations in the frequency range of 8-12 Hz arising from synchronous and coherent electrical activity of cells in the human brain, see [1]. Alpha waves in EEG predominantly originate from the brain during wakeful relaxation with closed eyes. Thus by instructing the user to "open" or "close" the eyes a simple induced by instruction paradigm is established. This is also known as an Alpha Attenuation Test (AAT). |

Figure 3:
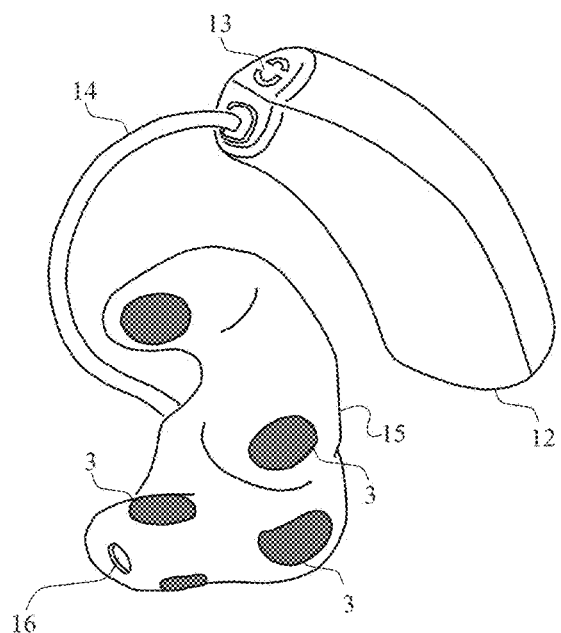
FIG. 3 illustrates an example of a device with integrated electrode validation, with electrodes arranged on an ear plug.

FIG. 3 shows a sketch of an embodiment of an EEG monitor device. The device is a behind-the-ear style device which is well-known from hearing aids. Typically it comprises a behind the ear part 12 with battery, electronic circuit and a microphone. The device 1 further comprises an ear-piece 15 and a connecting wire 14 between the behind-the-ear part 12 and the ear-piece 15. The electrodes are placed on the surface of a custom made ear-piece. The sound outlet 16 shown on the ear-piece provides the acoustical stimuli, generated by the device, to the user. The speaker (or receiver) of the device may be placed in the behind-the-ear part 12 and then connected to the ear-device through a sound tube, or the speaker may be placed in the ear-piece. The sound-outlet 16 may also provide an acoustical feed-through (vent) in order not to occlude the ear. The wire/sound-tube is a sound-guide in the case where the speaker is placed in the behind-the-ear device. If the speaker is placed in the ear-piece the wire/sound-tube is an electrical wire. The signal acquisition, i.e. pre-amplifier and analogue-to-digital converters (ADC's), may be placed in the ear-piece 15 or in the behind-the-ear part 12. The behind-the-ear part 12 may comprise a microphone for the purpose of measuring the sound pressure level of the user's environment. In this way the sound level from the device can be adapted to the sound pressure level of the user's environment. This may be advantageous both with respect to the audio stimuli for the electrode test, and for audio messages from the device to the user.

Figure 4:
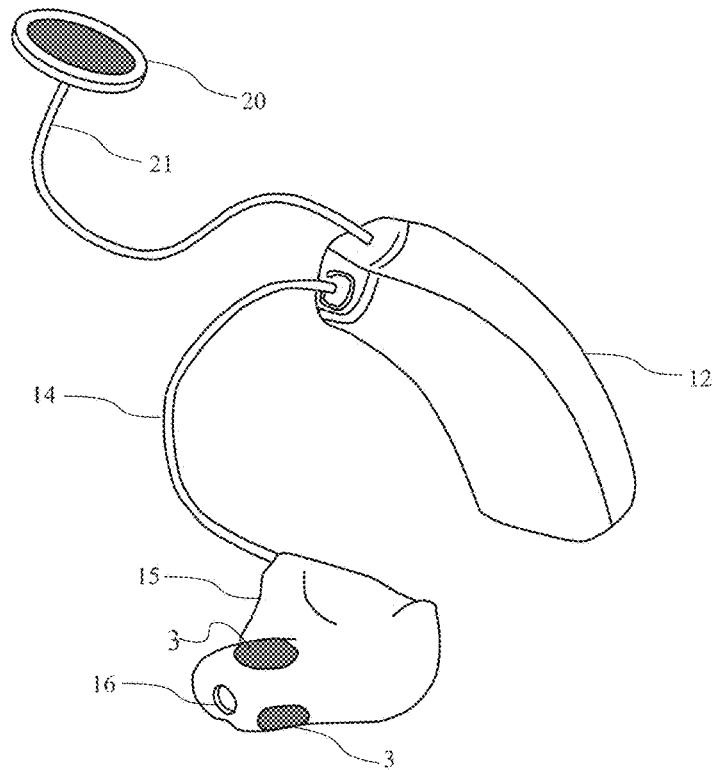
FIG. 4 illustrates a further example of a device with integrated electrode validation, with a further pad electrode.

FIG. 4 shows a further embodiment of an EEG monitor device 1. The device has electrodes 3 on the ear-piece 15 as the embodiment of FIG. 3, but is also provided with a pad electrode 20 connected to the behind-the-ear part 12 through a wire 21. Such a pad electrode can be arranged on the skin surface of the head in a point outside the ear canal. This can be relevant for surveillance of conditions where the EEG signal from a given region of the brain is relevant, and the signal obtainable from the ear canal is not sufficient.

In the practical implementation of the invention the electrodes may also be placed at e.g. the surface of a housing for the electronics, e.g. a behind-the-ear part 12.

Figure 5:
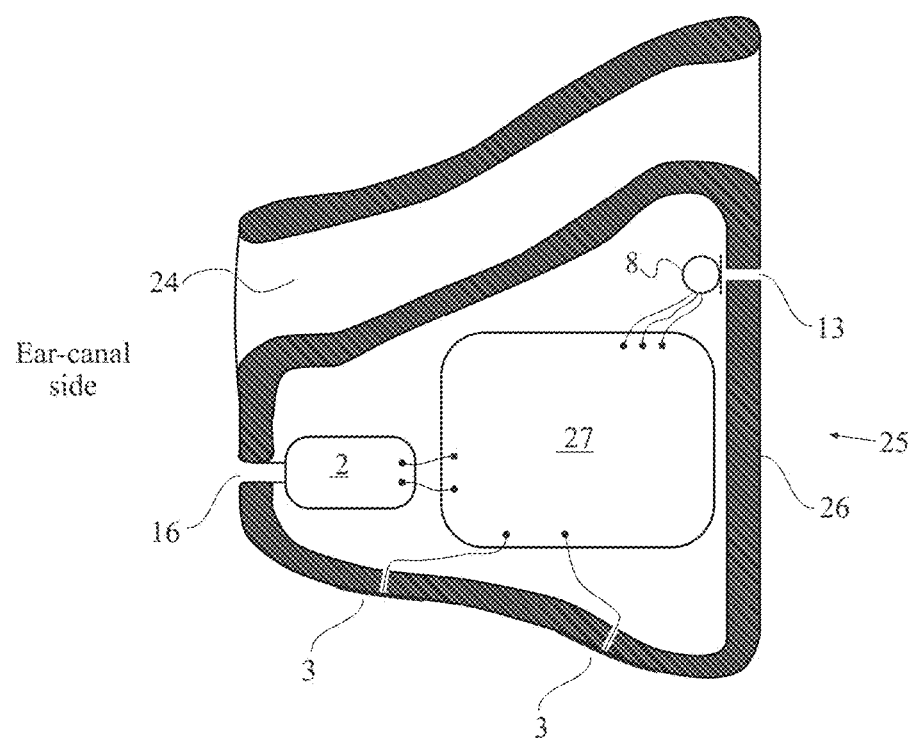
FIG. 5 illustrates a completely in-the-ear-canal device.

FIG. 5 shows a completely in-the-ear embodiment of an EEG monitor device in a cross sectional view. The device is housed in a custom made ear piece 25 as known from in-the-ear hearing aids. The contours of the outer surface 26 of the ear piece are manufactured to follow the contours of at least part of the ear canal and the concha of the user. The electrodes 3 are embedded in the part of the ear piece 25 outer surface 26 that is matched to follow the ear of the user. The device also comprises an electronic module 27 e.g. comprising different blocks of FIG. 1 or 2, a microphone 8 and a speaker or receiver 2. The sketch shows electrical wires connecting the electrodes 3, the microphone 8 and the speaker 2 with the electronic module 27. The electronic module comprises means for data acquisition, signal analysis and electrode validation. The ear piece has a ventilation channel 24 for the purpose of avoiding acoustical occlusion of the user's ear-canal i.e. blocking of the ear canal. Further the ear piece has an opening 13 for the microphone 8 and an opening 16 for the receiver 2.

Figure 6:
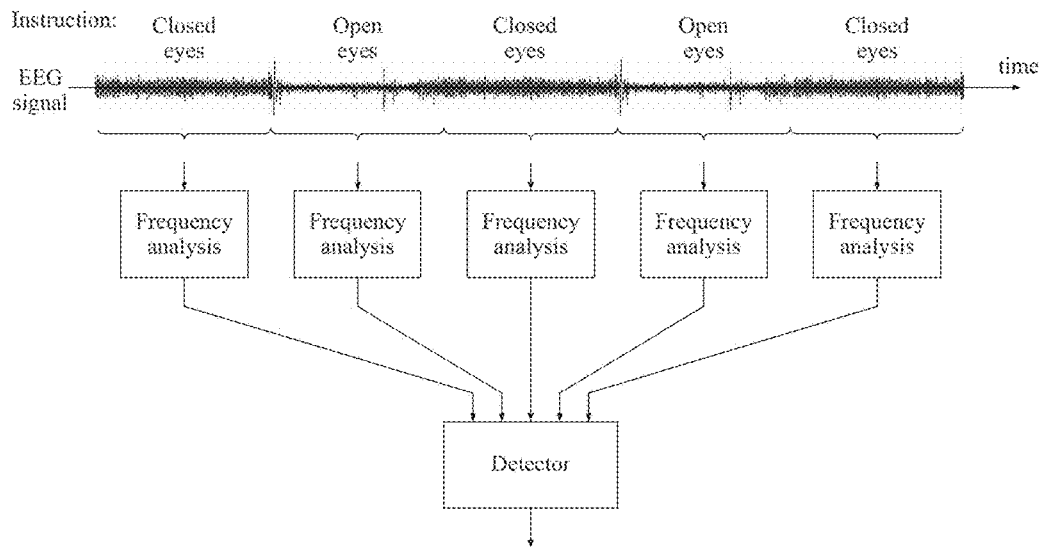
FIG. 6 illustrates initial signal analysis of different time periods.

FIG. 6 shows a layout for the alpha-band detection scheme. This could be applied when the electrode validation is based on an open/closed eye scheme. Instructions are given to the person through the speaker (receiver) 2. The instructions may be that the eyes should be closed, and after a given period the instruction could be that the eyes should be open. This could be repeated for a number of cycles. For each cycle the frequency analysis of the EEG signal is performed separately.

Alpha waves in EEG predominantly originate from the brain during wakeful relaxation with closed eyes. By instructing the user to "open" or "close" the eyes a simple induced by instruction paradigm is established. Thus by comparing the frequency distribution between open eyes epochs and closed eyes epochs it is possible to make a reliable and robust electrode test.

Figure 7:
FIG. 7 illustrates three different examples of block diagrams for the frequency analysis blocks in FIG. 6.
Figure 7:
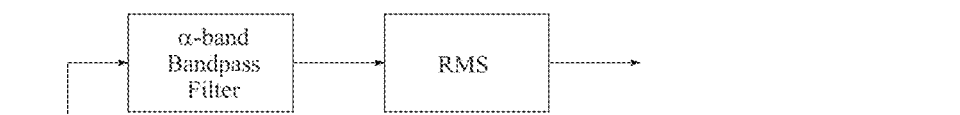
Figure 7:
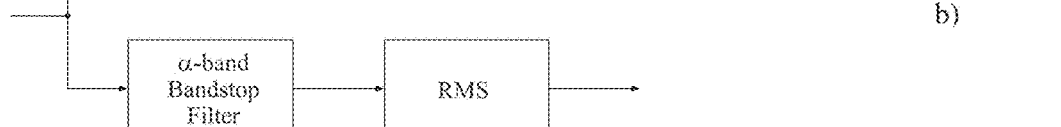

FIG. 7 shows three examples of block diagrams for the frequency analysis blocks in FIG. 6. The alpha-band band-pass filter in FIG. 7.*a* has a pass band in the 8-12 Hz frequency range. The second block in FIG. 7.*a* is a first norm or the absolute value of the signal. The lowpass filter in FIG. 7.a is averaging the signal. This lowpass filter could be a first or second order recursive filter.

In FIG. 7.b there are two branches where the top branch finds the energy in the alpha band and the branch below finds the energy outside the alpha band. The first block in the top branch is a bandpass filter allowing frequencies in the alpha band to pass. The first block in the branch below is a bandstop filter blocking frequencies in the alpha band but allowing other frequencies to pass. The second block in both branches in FIG. 7.b calculates the Root Mean Square of the signal.

FIG. 7.c shows an embodiment of a Short Time Fourier Analysis. The first block, Warped Delay Line, is a known method for changing the frequency scale in order to obtain a better resolution at low frequencies.

Figure 8:
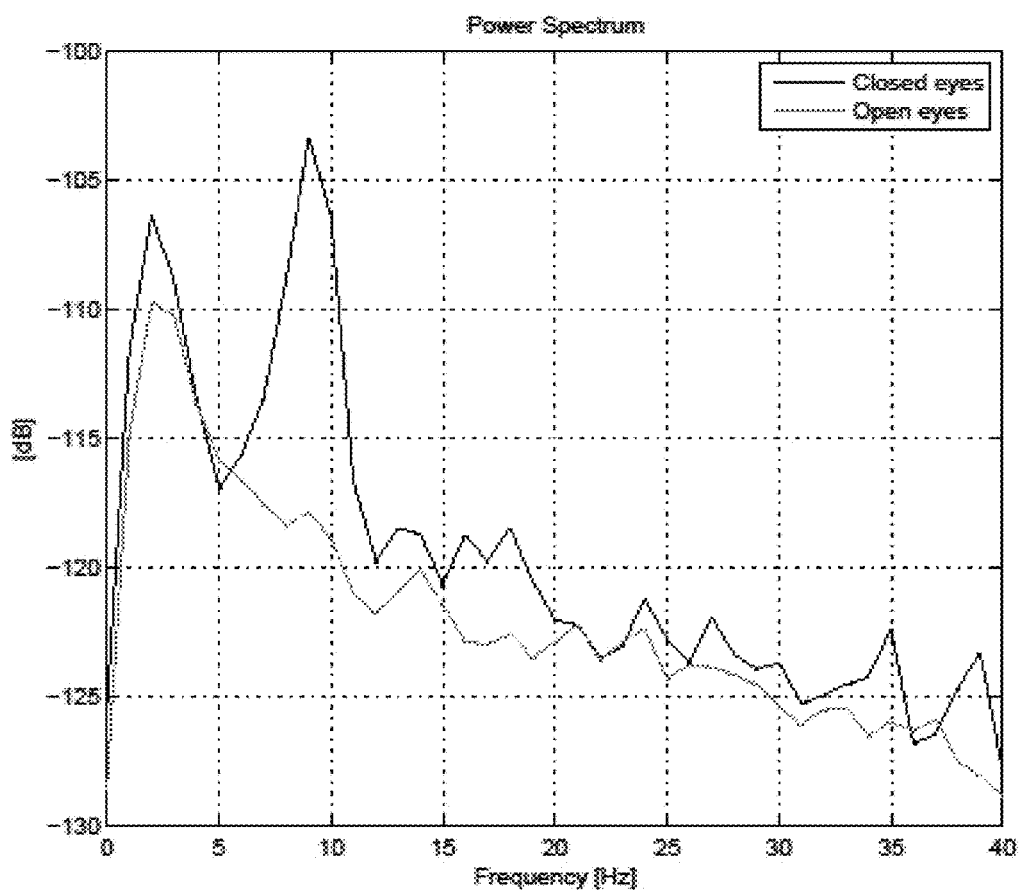
FIG. 8 illustrates example of power spectrum for EEG sampled with eyes closed and open, respectively.

FIG. 8 shows Power Spectrums from an in-the-ear type Ag-electrode. The signal is sampled at 512 Hz. In the first 30 seconds the person has the eyes closed and in the next 30 seconds the person has the eyes open. The two curves show the Power Spectrum for the first and the second 30 seconds time windows. The Power Spectrum is computed using the Welch method with window length 512 samples, Hamming-window, and 50% overlap between windows. There is a clear difference between the "open eyes" and "closed eyes" power spectrum in the alpha band (frequency range of 8-12 Hz).

Figure 9:
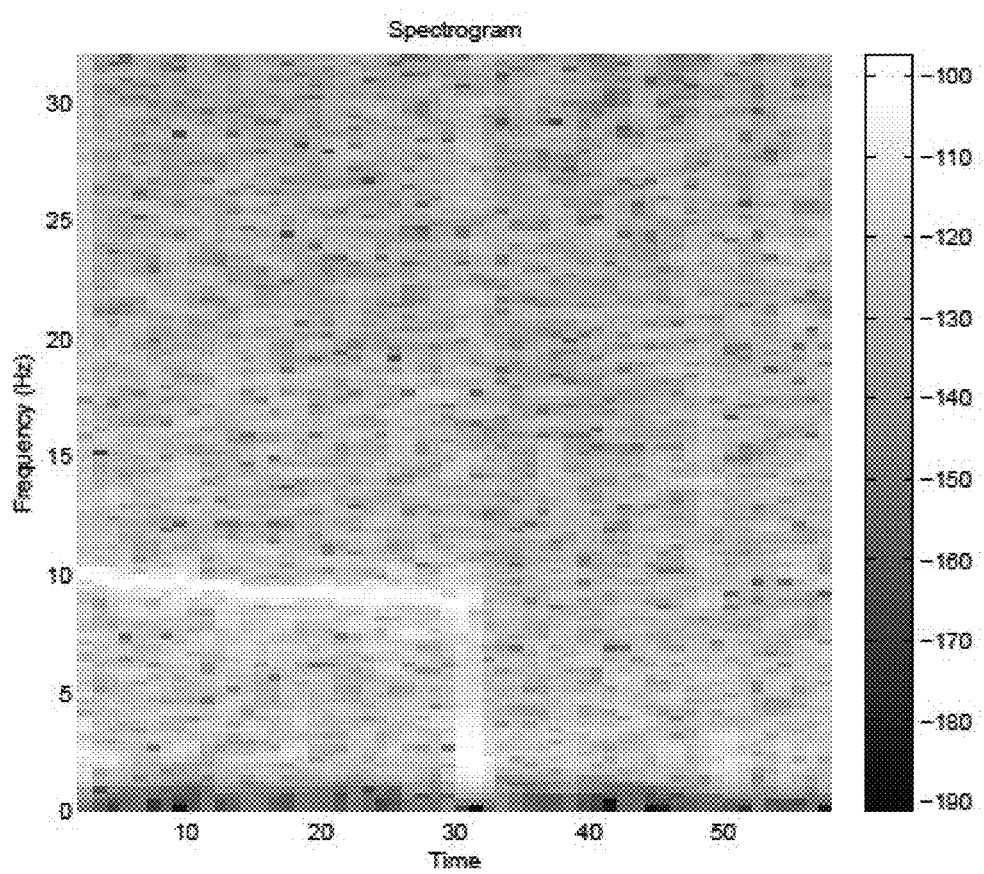
FIG. 9 illustrates a time frequency plot of the signal analyzed in FIG. 8.

FIG. 9 shows the time frequency plot for the same signal as in FIG. 8 but re-sampled to 64 Hz sample rate. The spectrogram is computed using the Short Time Fourier Transform (STFT), 512 samples in each window, and 64 new samples in each STFT. There is a clear increase of signal level in the alpha band for the open eye sequence compared to the closed eye sequence.

Figure 10:
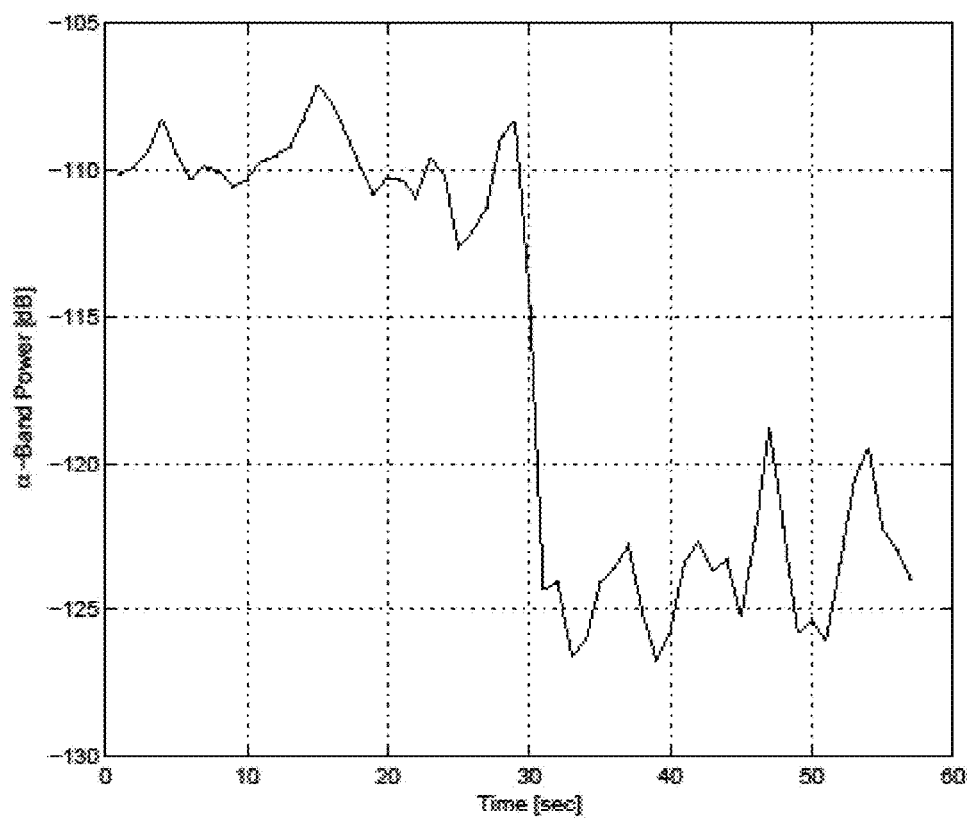
FIG. 10 illustrates the mean values of the frequency components in the alpha band, i.e. the mean value of a subsample of the second axis in FIG. 9.

FIG. 10 shows the same signal as in FIGS. 8 and 9. The curve shows the power of the alpha band (8-12 Hz) computed from the corresponding taps of the STFT from the spectrogram shown in FIG. 9. The curve shows a significant drop in alpha band power at 30 seconds, where the eyes are opened.

Figure 11:
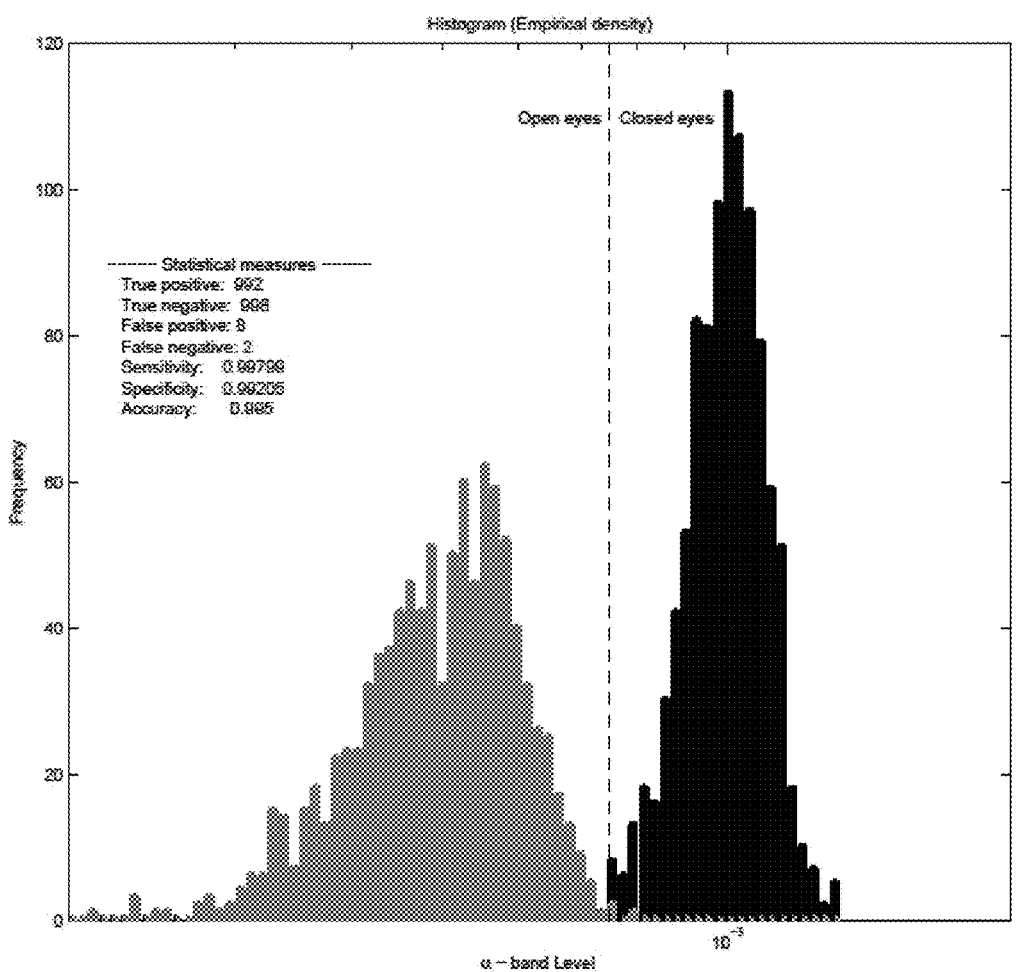
FIG. 11 illustrates a histogram of the alpha band power of the signal analyzed in FIG. 8, i.e. a histogram of the signal in FIG. 10.

FIG. 11 shows a simple one dimensional binary classifier for the alpha band detection scheme. The grey bars represent the histogram for the power in the alpha-band for the "Open eye" data, and the black bars represent the histogram for the "Closed eye" data. The dashed line shown is the discrimination level which results in the classification performance printed in the small table in the left part of FIG. 11. It is seen from this table that the specification and the accuracy are relatively good, implying that two measurements usually will be sufficient.

Figure 12:
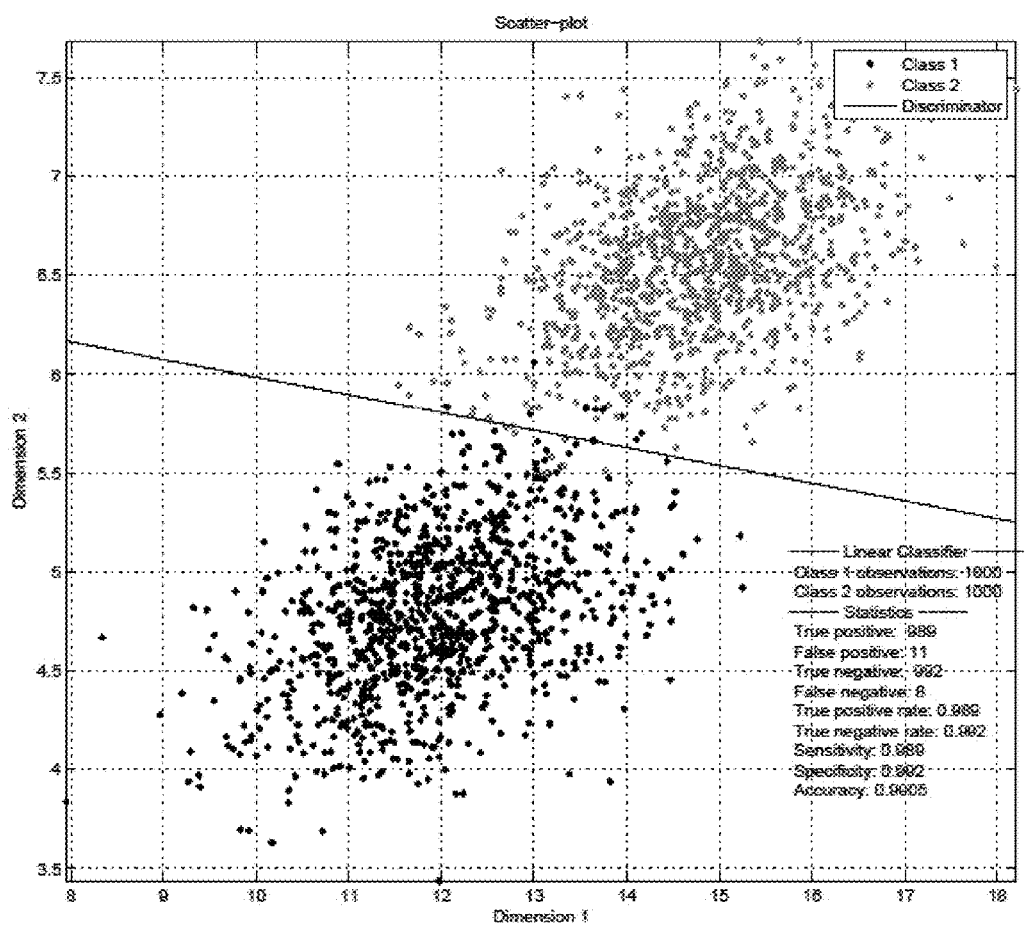
FIG. 12 illustrates a constructed example of a two dimensional classifier.

FIG. 12 shows a depiction of a two dimensional binary classifier for the alpha band detection scheme. The plot is a scatter plot where the dots represent data points in the feature space (dimension 1 versus dimension 2), and the solid line is the linear discrimination line. The black and gray dots represent data points from class 1 and 2 respectively. FIG. 12 shows a simulation example where the detector has two inputs; e.g. dimension 1 is the power from the alpha band and dimension 2 is the power from all other frequency bands. This could be obtained by the block diagram in FIG. 7.b where the top signal branch in FIG. 7.b provides dimension 1, and the below signal branch in FIG. 7.b provides dimension 2. In this example "Class 2" would be the "Closed eye" data and "Class 1" would be the "Open eye" data. This can be further generalized to non-linear classifiers, and to higher order linear or nonlinear classifiers.

The electrode validation may also be performed by a combination of different methods. E.g. the method based on generated audio-stimuli and the method based on ambient sounds may be combined. One example of such a combined system could be that the electrode test based on generated audio signals is performed when the device is switched on or whenever the user requests an electrode test. The electrode test based on the ambient sound environment will run continuously whenever the device is in use. The methods based on induced responses may also be combined with electrical impedance measurements. The advantage of combining different measurement methods is that this may improve the electrode validation in terms of reliability, robustness, the ability to distinguish between different fault causes etc.

Electrode validation based on electrical impedance measurements can also be implemented to be active continuously and at the same time as when measuring EEG signals. This is possible if the electrical signal applied to the electrode for measuring the impedance is in a frequency range outside the frequency range where the EEG signal is of interest. Typically the electrical signal can have a higher frequency, such as 500 Hz or more, than the frequency range where the EEG signal is of interest. Alternatively to selecting a different frequency for the impedance measurement, the EEG monitoring could be interrupted for a short period while the impedance measurement is performed. In that case the frequency of the impedance measurement could typically be in the range 10-30 Hz.

In the event that the electrode validation system cannot establish that the electrodes receive an EEG signal a notification could be given to the person wearing the EEG monitor. This will enable the person to adjust the position of the EEG electrodes in order to make sure that there is a good electrical connection between the electrodes and the skin. The notification could be in the form of a sound message, e.g. a voice message informing the person what to do.

We claim:

1. A wearable EEG monitor adapted to be carried at the head of a person, said EEG monitor comprising
    an EEG sensor part having skin surface electrodes configured to be located in an ear canal of said person for measuring an EEG signal from said person,
    an EEG signal analyzer configured to receive an EEG signal transferred from said EEG sensor part, and adapted for monitoring the EEG signal from said person,
    an EEG stimuli controller adapted for performing at least one of the following acts to establish a known stimulus suitable for causing an induced response:
        providing an auditory stimulus as said known stimulus to said person,
        requesting said person to perform a stimulus-creating act, or
        identifying an ambient sound suitable for acting as said stimulus,
    an EEG response detector for identifying said induced response from the EEG signal, and
    a classifier for performing an electrode validation by deciding based on said induced response if said skin surface electrodes are functioning to receive EEG signals of said person, whereby the electrode validation is based on a classification of said EEG signal from said person as either induced or not induced;
    wherein said monitor is a wearable personal device configured to be continuously worn by said person for long term monitoring of EEG signals.

2. The EEG monitor according to claim 1, wherein the electrodes are dry electrodes.

3. The EEG monitor according to claim 1, wherein said EEG stimuli controller provides said stimulus to said person and said stimulus is an auditory stimulus.

4. The EEG monitor according to claim 1, wherein said EEG stimuli controller identifies said suitable ambient sound by identifying sounds from the surroundings capable of causing an induced response.

5. The EEG monitor according to claim 1, wherein said EEG stimuli controller requests said person to perform a stimulus-creating act by requesting said person to open and close the eyes.

6. The EEG monitor according to claim 1, wherein said EEG stimuli controller provides said stimulus by repeating said stimulus at least two times.

7. The EEG monitor according to claim 1, wherein at least one of said skin surface electrodes is arranged on an ear-piece, said ear-piece being customized for fitting the ear canal of said person.

8. The EEG monitor according to claim 7, further comprising a pad electrode external to said ear-piece, said pad electrode adapted to be arranged on the head of the person to be monitored.

9. The EEG monitor according to claim 1, adapted for validating at least three of said skin surface electrodes simultaneously, based on said identification of said induced response.

10. The EEG monitor according to claim 9, wherein said validation of electrodes by identifying said induced response is combined with measuring an electrical impedance between a plurality of said skin surface electrodes.

11. The EEG monitor according to claim 1, comprising a notification component responsive to the decision of said classifier for notifying said person if the EEG signal is not received.

12. The EEG monitor according to claim 1, comprising an EEG electrode identification component responsive to the decision of said classifier for identifying electrodes receiving an EEG signal and selecting these electrodes for monitoring the EEG signal from said person.

13. The EEG monitor according to claim 1, comprising a wireless transmitter which transmits a wireless notification to an external unit in response to the absence of a decision by said classifier that the EEG signal is received by the electrodes.

14. The EEG monitor according to claim 1, wherein said skin surface electrodes have an electrode impedance of at least several hundred kilo ohms.

15. The EEG monitor according to claim 1, further comprising an acoustic signal generator and a speaker responsive to said acoustic signal generator for producing at least one of said stimulus or a request to perform said stimulus-creating act.

16. The EEG monitor according to claim 1, wherein said stimuli controller selectively performs different of said acts at different times.

17. A method for monitoring EEG signals of a person by an EEG monitor carried at the head of said person, said method comprising the steps of
measuring one or more EEG signals from said person by an EEG sensor part having skin surface electrodes configured to be located in an ear canal of said person,
transferring an EEG signal from said EEG sensor part to a processing unit having an EEG signal processor,
monitoring the EEG signal from said person in said processing unit,
establishing a known stimulus, suitable for causing an induced response in the EEG signal, by performing at least one of the following acts:
providing an auditory stimulus as said known stimulus to said person,
requesting said person to perform a stimulus creating act,
identifying an ambient sound suitable for acting as said stimulus,
identifying said induced response from the EEG signal, and
deciding, based on classification of said EEG signal from said person as either induced or not induced, if said skin surface electrodes are functioning to receive EEG signals of said person;
wherein said monitor is a wearable personal device configured to be continuously worn by said person for long term monitoring of EEG signals.

18. The method according to claim 17, comprising notifying said person if said electrodes are not determined to be functioning to receive EEG signals.

19. The method according to claim 17, comprising identifying the specific electrodes functioning to receive an EEG signal.

20. The method according to claim 17, comprising reconfiguring the EEG monitor to measure the EEG signal by selecting those electrodes functioning to receive an EEG signal.

21. The method according to claim 17, comprising repeating the steps of causing an induced response in the EEG signal and identifying an induced response from the EEG signal at time intervals either preselected or adjusted according to previous decisions if said electrodes are functioning to receive an EEG signal.

22. The method according to claim 17, wherein said skin surface electrodes have an electrode impedance of at least several hundred kilo ohms.

23. The method according to claim 17, wherein at least one of said providing or requesting steps is performed by an acoustic signal generator and a speaker responsive to said acoustic signal generator.

24. The method according to claim 1, wherein said monitor selectively performs different of said acts at different times.

* * * * *